(12) United States Patent
Chen

(10) Patent No.: US 11,871,810 B2
(45) Date of Patent: Jan. 16, 2024

(54) COMMUNICATION HELMET

(71) Applicant: Tai Hong Chen, Taipei (TW)

(72) Inventor: Tai Hong Chen, Taipei (TW)

( * ) Notice: Subject to any disclaimer, the term of this patent is extended or adjusted under 35 U.S.C. 154(b) by 595 days.

(21) Appl. No.: 16/926,461

(22) Filed: Jul. 10, 2020

(65) Prior Publication Data
US 2020/0383419 A1 Dec. 10, 2020

Related U.S. Application Data

(60) Provisional application No. 62/845,335, filed on May 9, 2019.

(51) Int. Cl.
*A42B 3/30* (2006.01)
*H04B 1/3827* (2015.01)
*A61B 5/024* (2006.01)
*H04W 4/02* (2018.01)

(52) U.S. Cl.
CPC ............. *A42B 3/30* (2013.01); *A61B 5/024* (2013.01); *H04B 1/385* (2013.01); *H04W 4/02* (2013.01); *H04B 2001/3866* (2013.01); *H04R 2460/13* (2013.01)

(58) Field of Classification Search
CPC .......... A42B 3/30; A61B 5/024; H04B 1/385; H04B 2001/3866; H04W 4/02; H04R 2460/13
See application file for complete search history.

(56) References Cited

U.S. PATENT DOCUMENTS

| 9,918,264 | B1* | 3/2018 | Bitra ..................... H04W 4/02 |
| 2009/0161893 | A1* | 6/2009 | Hironaka ............ H04M 1/6066 381/151 |
| 2017/0172243 | A1* | 6/2017 | Scripa .................... A42B 3/303 |
| 2018/0279962 | A1* | 10/2018 | Sane ..................... A61B 5/0531 |
| 2019/0034142 | A1* | 1/2019 | Uchikawa ............ H04N 1/0035 |
| 2019/0191813 | A1* | 6/2019 | Liu ........................ A42B 3/066 |

FOREIGN PATENT DOCUMENTS

| CN | 109876321 A | * | 6/2019 |
| CN | 209995435 U | * | 1/2020 |

* cited by examiner

*Primary Examiner* — Mohammed Rachedine
(74) *Attorney, Agent, or Firm* — Chun-Ming Shih; LANWAY IPR SERVICES

(57) ABSTRACT

A communication helmet includes a helmet, a fixing belt, and a speaker module. The helmet has a head cavity for protecting a human head. Such helmet may be any known or new types of helmets for protecting soldiers, riders, policemen, working men in architecture building or in another engineering facilities, or for any other purposes and uses. The fixing belt has two belt ends connecting to two sides of the helmet. The fixing belt and the helmet together form a head container for fitting the human head.

20 Claims, 5 Drawing Sheets

COMMUNICATION HELMET

RELATED APPLICATION

The present application claims priority of provisional application No. 62/845,335.

FIELD

The present application is related to a helmet device and more particularly related to a helmet device with communication function.

BACKGROUND

Communication is important for a team work, no matter it is used in a bicycle racing team, mountain climbers, or soldiers in a war. In a racing field or a battle field, however, there is lots of environment noise and thus making effective audio communication very difficult to achieve. Visual signs or sign languages still have certain limitations on expressing ideas and transmitting messages.

Therefore, it is beneficial to create an effective and convenient way to provide better communication among people.

SUMMARY OF INVENTION

According to an embodiment, a communication helmet includes a helmet, a fixing belt, and a speaker module. The helmet has a head cavity for protecting a human head. Such helmet may be any known or new types of helmets for protecting soldiers, riders, policemen, working men in architecture building or in another engineering facilities, or for any other purposes and uses.

Such helmet may cover a part of a head, e.g. a back side of the head. Such helmet may also have a transparent plastic shield covering face of a head. The material of the helmet may be material, bullet-proof fiber, plastic or other materials suitable for the design requirements of the helmet.

The fixing belt has two belt ends connecting to two sides of the helmet. The fixing belt and the helmet together form a head container for fitting the human head. Usually, the face of the human head is exposed while back skull is covered and protected by the helmet. The fixing belt may have two detachable parts attached together when wearing the communication helmet. The fixing belt may also be a belt that may be adjusted for its length to fasten the wearing of the helmet. It is also covered in the invention to have more than two belt ends fixing to the helmet.

The speaker module is disposed on the fixing belt. The speaker module has a processor, a bone conductive speaker and a contact part. The contact part engages a cheek of the human head when the human head is fit in the head container of the helmet and the fixing belt. The bone conductor speaker emits a vibration wave corresponding to associated sound data from the processor. The vibration wave is transmitted to an acoustic organ of the human head via the contact part for transmitting information carried by the sound data to the human head.

In some embodiments, the processor may have a controller or a processor unit that can execute program codes or even operating systems. The speaker module may be a stand alone device that can be used independently.

In some other embodiments, the processor may include a wireless circuit or other communication circuit for operating together with one or more other devices. For example, there may be a host device sending instructions, data and other information to the processor. Such design may reduce the size and weight of the speaker module.

The speaker module has a contact part, which may directly or indirectly engage the cheek of the person who wears the communication helmet. As mentioned above, the fixing belt is used for fixing the helmet to the human head. When the fixing belt is fastened, it may have two lateral sides engaging the cheek of the human head. The contact part of the sensor module that is attached to the fixing belt engages the cheek for sending the vibrating wave of the bone conductor speaker to the acoustic organ of the human head so that the person who wears the bone conductive speaker can hear sounds corresponding to the vibrating wave.

In other words, the processor generates vibrating wave data that are converted to the vibrating wave. The vibrating wave data may be generated from sound data collected from a local microphone, from a host device as mentioned above, or from multiple sources and mixed together or in multiple channels.

An application for the communication helmet is used in a battle field. The sound data may refer to raw sounds in the battle field, or amplified, filtered sounds in the battle field, audio communication from team mates, or artificially generated information converted into acoustic data to be heard by the person who wears the communication helmet. The acoustic data may be speech data or just sound, like indication of a closing enemy like a tank, a closing person in the quiet dark night.

Another application for the communication helmet is for police men and women. Similarly, the helmet protects head of a police man or a police woman while the bone conductive speaker sends clear acoustic data to him or her while keeping his or her eyes open to environment sounds that are critical to keep him or her safe and get operation done successfully.

Other security workers that need helmets for protecting their safety in daily work are also welcomed for such communication helmet. Riders for motorcycles, bicycles may also wear such communication helmets so as to protect their safety and to provide additional information to them at the same time.

There may be one or more than one speaker module fixing to the communication helmet. The speaker module may be detached and replaced conveniently for different missions or requirements. Even without the speaker module, the communication helmet is still capable of protecting safety of the person who wears the communication helmet. On the other hand, when the person wears the communication helmet with the speaker module, the person does not need to wear an additional earphone, because the speaker module is already attached to the fixing belt of the communication helmet. When the person wears the communication helmet, he wears the conductive bone speaker at the same time.

Furthermore, the fixing belt, in the past, is only used for fixing the helmet to the person's head. The fixing belt has two lateral sides engaging cheeks of the person's head. When the speaker module is attached to the lateral side, the speaker module directly or indirectly contacts the cheek of the person. With that contact, the bone conductive speaker successfully sends vibrating waves to the person via the contacted cheek.

In some embodiments, the fixing belt includes an attaching structure for placing the speaker module and pressing the contact part of the speaker module to engage the cheek when the communicate helmet is worn on the human head. Such attaching structure may be a holder or a support for inserting the speaker module and for positioning the speaker module so that the bone conductive speaker engages the cheek directly or indirectly.

In some embodiments, the speaker module is connected to an environment microphone. The environment microphone collects an environment sound. An event message is generated by recognizing the environment sound and transmitted to the human head via the bone conductor speaker.

For example, the environment microphone may be integrated in the speaker module. In such case, the environment microphone collects sounds and the speaker or a connected host device processes the sounds like filter, recognize, amplify the sounds. In some embodiments, the sounds like gunshot may be filtered and recognized to find out which gun type is related to the gunshot sound. A distance or other event message may be converted corresponding sound sent to the person who wears the communication helmet. For example, "there is a gunshot at 11 o'clock position, which may be a AK-47 from an enemy" may be sent to a soldier or a policeman.

Under current sound recognition, other information may also be collected and generated based on raw data. This is particularly helpful for a soldier or a police man in a battle field. This is also helpful for a bicycle rider to be aware of an approaching car from behind.

The sound collected from a person's communication helmet may be sent to another communication helmet for processing together. In some other cases, multiple sound sources may be processed together to find more useful information therefrom.

A portable computer may be used for handling such processing, or the data are sent to a cloud server. Because current technology makes a mobile phone capable of processing complicated sound recognition, a distribution computation or a standalone computation may also be used, depending on different design needs.

In some embodiments, the event message is related to an explosion sound, as mentioned above. A helicopter, a tank, a ship, a closing car or other objects may also be put into an interest group to be analyzed.

By placing two sound collector devices like microphones, a position relative to the communication helmet may be estimated, just like human ears for detecting positions of a sound source.

In some embodiments, the communication helmet further includes an external device working with the processor for recognizing the environment sound. As mentioned above, the external device may be a portable host device also carried by the person who wears the communication helmet or may be another portable device held by another person or even a cloud server located in a distant place.

In some embodiments, the environment sounds collected by a plurality of the communication helmets are integrated with position data of the plurality of the communication helmets to determine an absolute position associated to the explosion sound. The absolute position is translated to multiple relative positions embedded in the event messages for the plurality of the communication helmets.

As mentioned above, a team of soldiers may each wear a communication helmet. These communication helmets may collect sounds or other information separately and then these information is exchanged among the communication helmets. By adding GPS (Global Positioning System) devices for providing absolute position information for multiple people who wear the communication helmets, the absolute positions of these people are analyzed by reference to sounds collected by multiple communication helmets and converted to relative information, e.g. "a gunshot at 11 o'clock" for a specific solder wearing the communication helmet.

Map information may also be integrated so that the audio information has map information like, "move right, there is a place to hide. A gunshot is from a left side forrest."

For military use, a set of communication helmets may be grouped and connected with a closed network, instead of communication over a public network. The processor may be operated over more than one networks and one of the networks may be a closed network only accessible by the communication helmets. The closed network is operated over encrypted technology so that other unauthenticated devices are unable to access data of the closed network.

The processor may have a manual switch for entering the closed network when a mission is activated and entering a relative public network when the mission is finished.

In some embodiments, the communication helmet may also include a pulse detector connected to the processor for collecting heart pulse information of the human head. With such design, a team commander may have health information of his team members. The heart pulse information may be transmitted to another communication helmet.

In some embodiments, the processor provides an operation interface for setting a role in a team to the processor. The processor functions differently for different roles. For example, the speaker modules may be manually set and assigned to different team members. These team members may each have a different role, e.g. a captain or a shooter, and these communication helmets may be used with different functions and/or communication path settings, e.g. the communication topology, whose information should be transmitted to whose communication helmet.

In some embodiments, the processor includes a wireless circuit for processing wireless signals.

In some embodiments, the processor is selectively switched from multiple networks.

In some embodiments, there may be a manual switch for disabling a part of the multiple networks.

In some embodiments, a part of the multiple networks is disabled by sending a remote command to the processor. For example, when a soldier is dead, his helmet may be picked and used by an enemy. In such case, the communication helmet may be disabled for protecting other team members.

In some embodiments, the speaker module includes a microphone for collecting audio data from the human head.

The processor may also count how many bullets have been used and tell the soldier how many bullets are stilled existed.

In some embodiments, the audio data are converted to instructions, and the processed result of the instructions is replied via the bone conductive speaker. For example, a soldier, a rider or a police man may speak to issue commands, e.g. to turn on a machine, and the bone conductive speaker is used for sending feedback information, e.g. the machine is activated, to the person who wears the communication helmet.

In some embodiments, the processor handles wireless communication and data conversion for the bone conduction speaker.

In some embodiments, the helmet has a battery container for containing a battery supplying power to the speaker module. In such design, it is more comfortable when the speaker module has a less weight when its battery is moved and placed and protected in the helmet.

In some embodiments, the fixing belt has an electrical wire supplying power to the speaker module. In such design, the fixing belt may be woven or attached with power or signal lines used by the speaker module.

In some embodiments, biophysical data of the human head are collected as an authentication to operate the processor of the speaker module. For example, a radar wave may be sent to the human head of the person who wears the communication helmet and the response is used for authenticating the identity of the person.

One use of such function is to prevent unauthenticated users to use the communication helmets. Another use of such function is to dynamically correspond the communication helmet with the person who wears the communication helmet.

In addition to use vibrating wave to detect user head identity, optical image analysis may also be used for finding identify of the person who wears the communication helmet.

In some embodiments, the biophysical data are used for decrypting messages of the processor, e.g. as a key in a decryption computation or to encrypt communication information.

In some embodiments, the communication helmet may have an identification unit, like a card to be inserted into the sensor module or a RFID carrying a wireless information to be accessed by the speaker module, connected to a detachable identification module. The detachable identification module is attached to the speaker module for providing an identification message for the communication helmet.

In some embodiments, the processor selects at least one channel from multiple channels to generate the vibration wave. In other words, the processor may receive multiple channels and dynamically mix some of the channels converting to vibrating waves from the bone conductive speaker.

Another aspect of the invention is to provide a helmet speaker apparatus that has a contact part for engaging a cheek of a human head, a processor for providing sound data, and a bone conductor speaker connected to the contact part and the processor for generating a vibration wave corresponding to the sound data. The vibration wave is transmitted to a acoustic organ via the contact part and the cheek. The helmet speaker apparatus also has a module housing for being attached to an attaching structure of a fixing belt. The fixing belt has two belt ends connected to a helmet. The fixing belt and the helmet form a head container for fitting and protecting the human head.

The module housing may be water proof designed, with some exposed electrodes to be connected to a power source or to another device to work together.

Even without wearing the helmet, users may engage the helmet speaker apparatus to his cheek to hear sounds. With such design, it is easier to provide a robust design, or makes it more convenient to charge or replace when the helmet speaker apparatus is temporarily out of order.

Another aspect of the invention is to provide a battle field information system. The battle field information may include multiple communication helmets. Each communication helmet includes a helmet, a fixing belt and a speaker module, the speaker module being placed on the fixing belt with a contact part engaging to a cheek of a human head, a bone conductor speaker transmitting a vibrating wave corresponding to battle field data via the contact part to an acoustic organ of a human head wearing the communication helmet. A network device is used for the multiple communication helmets to communicate for utilizing environment sounds collected by the multiple communication helmets and dispatching environment messages via the bone conductor speakers of the multiple communication helmets.

DETAILED DESCRIPTION

Figure 1:
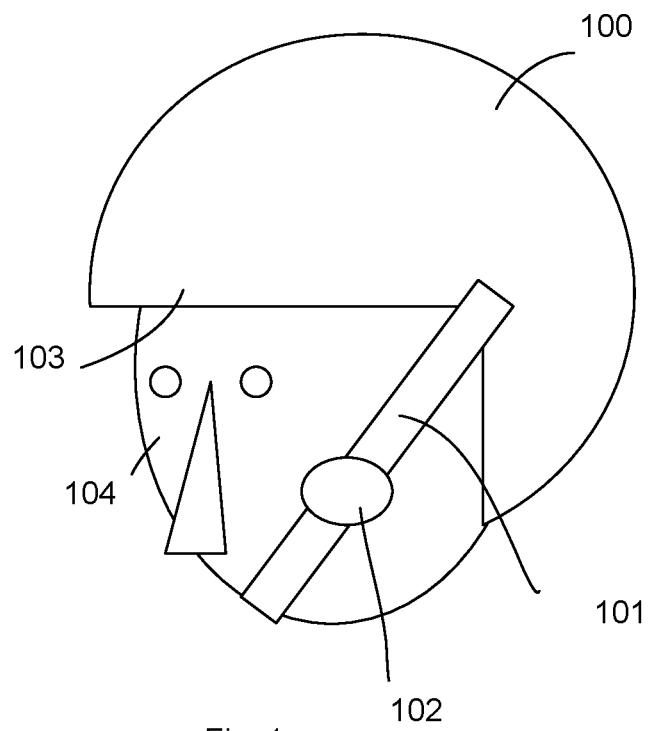
FIG. 1 illustrates a helmet example.

In FIG. 1, a communication helmet includes a helmet 100, a fixing belt 101, and a speaker module 102. The helmet 100 has a head cavity 103 for protecting a human head 104. Such helmet 100 may be any known or new types of helmets for protecting soldiers, riders, policemen, working men in architecture building or in another engineering facilities, or for any other purposes and uses.

Such helmet may cover a part of a head, e.g. a back side of the head. Such helmet may also have a transparent plastic shield covering face of a head. The material of the helmet may be material, bullet-proof fiber, plastic or other materials suitable for the design requirements of the helmet.

Figure 2:
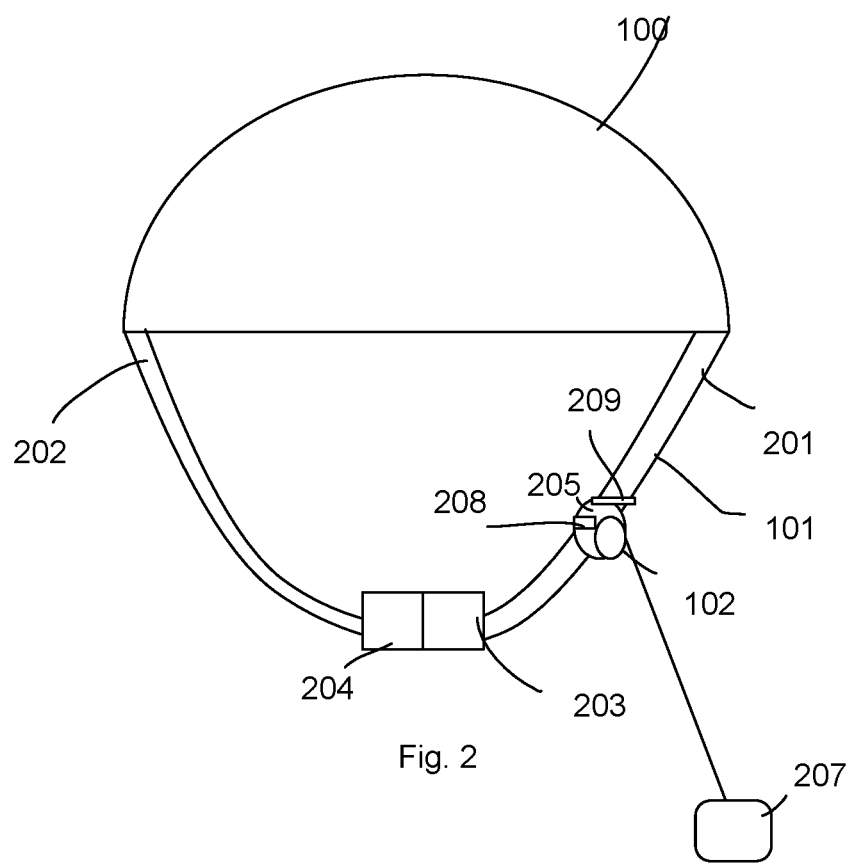
FIG. 2 illustrates another view of the example.

In FIG. 2, the fixing belt 101 has two belt ends 201, 202 connecting to two sides of the helmet 100. The fixing belt 101 and the helmet 100 together form a head container for fitting the human head. Usually, the face of the human head is exposed while back skull is covered and protected by the helmet. The fixing belt 101 may have two detachable parts 203, 204 attached together when wearing the communication helmet. The fixing belt 101 may also be a belt that may be adjusted for its length to fasten the wearing of the helmet. It is also covered in the invention to have more than two belt ends fixing to the helmet.

In FIG. 1 and FIG. 2, the speaker module 102 is disposed on the fixing belt 101.

Figure 3:
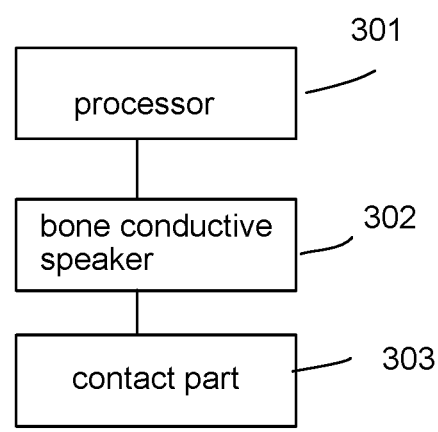
FIG. 3 illustrates a circuit structure of an embodiment.

In FIG. 3, The speaker module has a processor 301, a bone conductive speaker 302 and a contact part 303. The contact part 303 engages a cheek of the human head, as illustrated in FIG. 1, when the human head is fit in the head container of the helmet and the fixing belt. The bone conductor speaker 302 emits a vibration wave corresponding to associated sound data from the processor 301. The vibration wave is transmitted to an acoustic organ of the human head via the contact part 303 for transmitting information carried by the sound data to the human head.

To keep the helmet fitting on the head of a user, the belt is fastened and attach to surface of the cheek of the user. The contact part may be placed facing to the cheek. In some embodiment, the contact part has protruding structure protruding from an inner surface of the belt for better contacting the cheek of the user.

Figure 4:
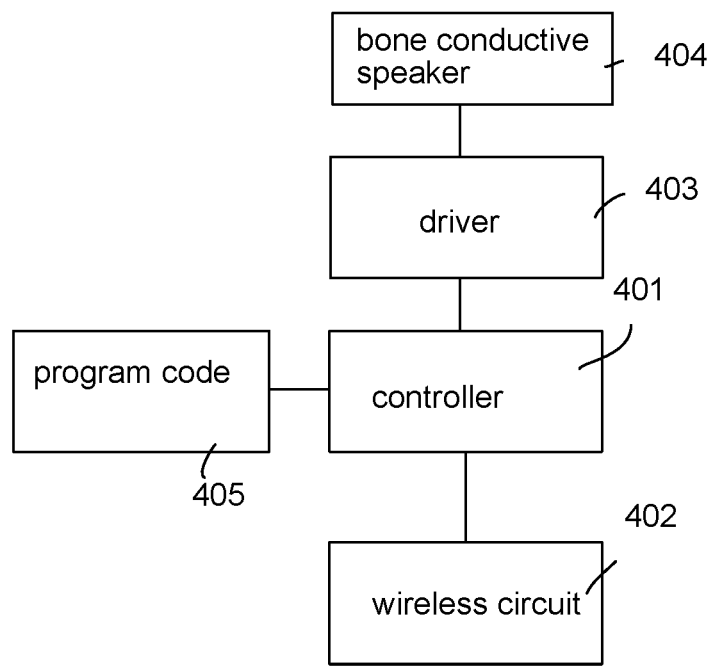
FIG. 4 illustrates a detailed diagram of a speaker module structure.

In FIG. 4, the processor may have a controller 401 or a processor unit that can execute program codes 405 or even operating systems. The controller 401 decodes the audio data received from the wireless circuit 402, which receives signal from an external audio source, like a microphone device from another place. The decoded data are converted to driving current by the driver 403 and control signals sending to the bone conductive speaker 404 to generate the vibration wave.

The audio data may be processed by digital signal processing techniques to remove echo, noise. In addition, the program code 405 may be encoded or the controller 401 itself is designed to enhance or amplify certain voice, e.g. human voice.

The speaker module may be a stand alone device that can be used independently. Specifically, the speaker module may be detached from the belt. Furthermore, the speaker module may be detached from a helmet and attach to another helmet. This is particularly important in the war field. When a soldier is dead, the speaker module may be disable firstly by detecting life signals like heart vibration first to prevent enemy to use the speaker module to get information. Another friend soldier in the battle field, on the other hand, may get the speaker module to place in his helmet after the speaker module authenticates the identity of the friend soldier by biological information, like finger print pre-stored in the speaker module, and then activates operation again.

Moreover, the speaker module, when detects the identity of the friend soldier, the audio data may be re-routed to provide more accurate information.

For example, each speaker module may be associated with a soldier. In the war field, a command may be sent to a set of soldiers. Only soldiers in the set hear the audio data via the speaker module, although the audio data may be received by the wireless circuit.

This can be made by adding receivers via audio recognition technology. For example, when a leader speaks "to alpha team", the following commands are only sent to soldiers in the alpha team. For soldiers in the beta team do not receive the command, even their wireless module receives the broadcasted audio data for the controller may filter unwanted data from received data.

This increases communication efficiency compared to a broadcast scheme. A receiver is assigned via audio recognition first, and then the following data are transmitted to assigned receivers.

Figure 5:
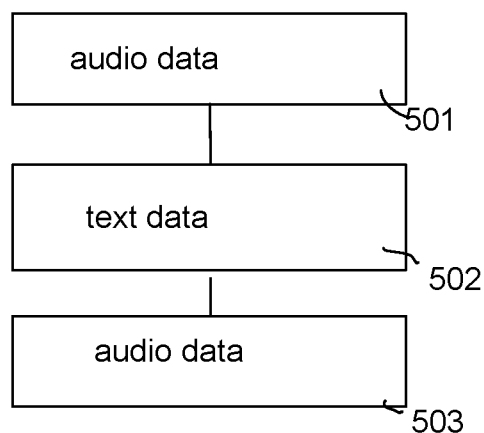
FIG. 5 illustrates a data conversion scheme.

In FIG. 5, audio data 501 are firstly said by a sender. The audio data 501 is converted to text data 502 via audio recognition and sent to a speaker module of a receiver. The speaker module receives the text data 502 and reconstruct the audio data 503 in the speaker module based on the text data 502.

For example, the audio data "Help, I am at floor 7" are firstly processed and converted to text data "Help, I am at floor 7." The text data, which consumes less network bandwidth, are transmitted over a wireless protocol.

When the text data consumes much smaller bandwidth, it may be encrypted and transmitted with much better efficiency and effect.

When the text data arrives at the speaker module of the receiver, the text data are converted to audio data via text to speech technology to render the audio data.

Furthermore, the rendered audio data may be added with more information. For example, the GPS data of the sender are also sent along with the text data to the receiver. The GPS data are also converted and added into the audio data. The controller may compute and compare the GPS data of the sender with the GPS of the receiver and the map, and add further helpful information to the rendered audio data.

For example, "Help, I am in the park" are converted and added with information "Help, I am Tom, I am in the part, 50 meters on your right side."

In other words, the rendered audio data 503 for generating corresponding vibration wave may be added with further information or removed for certain information.

The speaker module reconstruct and organize information for the user who wears the helmet and uses the speaker module.

In some other embodiments, the processor may include a wireless circuit or other communication circuit for operating together with one or more other devices. For example, there may be a host device sending instructions, data and other information to the processor. Such design may reduce the size and weight of the speaker module.

The speaker module has a contact part, which may directly or indirectly engage the cheek of the person who wears the communication helmet. As mentioned above, the fixing belt is used for fixing the helmet to the human head. When the fixing belt is fastened, it may have two lateral sides engaging the cheek of the human head. The contact part of the sensor module that is attached to the fixing belt engages the cheek for sending the vibrating wave of the bone conductor speaker to the acoustic organ of the human head so that the person who wears the bone conductive speaker can hear sounds corresponding to the vibrating wave.

In other words, the processor generates vibrating wave data that are converted to the vibrating wave. The vibrating wave data may be generated from sound data collected from a local microphone, from a host device as mentioned above, or from multiple sources and mixed together or in multiple channels.

An application for the communication helmet is used in a battle field. The sound data may refer to raw sounds in the battle field, or amplified, filtered sounds in the battle field, audio communication from team mates, or artificially generated information converted into acoustic data to be heard by the person who wears the communication helmet. The acoustic data may be speech data or just sound, like indication of a closing enemy like a tank, a closing person in the quiet dark night.

Another application for the communication helmet is for police men and women. Similarly, the helmet protects head of a police man or a police woman while the bone conductive speaker sends clear acoustic data to him or her while keeping his or her eyes open to environment sounds that are critical to keep him or her safe and get operation done successfully.

Other security workers that need helmets for protecting their safety in daily work are also welcomed for such communication helmet. Riders for motorcycles, bicycles may also wear such communication helmets so as to protect their safety and to provide additional information to them at the same time.

There may be one or more than one speaker module fixing to the communication helmet. The speaker module may be detached and replaced conveniently for different missions or requirements. Even without the speaker module, the communication helmet is still capable of protecting safety of the person who wears the communication helmet. On the other hand, when the person wears the communication helmet with the speaker module, the person does not need to wear an additional earphone, because the speaker module is already attached to the fixing belt of the communication helmet. When the person wears the communication helmet, he wears the conductive bone speaker at the same time.

Furthermore, the fixing belt, in the past, is only used for fixing the helmet to the person's head. The fixing belt has two lateral sides engaging cheeks of the person's head. When the speaker module is attached to the lateral side, the speaker module directly or indirectly contacts the cheek of the person. With that contact, the bone conductive speaker successfully sends vibrating waves to the person via the contacted cheek.

In FIG. 2, the fixing belt includes an attaching structure 205 for placing the speaker module 102 and pressing the contact part of the speaker module to engage the cheek when the communicate helmet is worn on the human head. Such attaching structure may be a holder or a support for inserting the speaker module and for positioning the speaker module so that the bone conductive speaker engages the cheek directly or indirectly.

In some embodiments, the speaker module is connected to an environment microphone. The environment microphone collects an environment sound. An event message is generated by recognizing the environment sound and transmitted to the human head via the bone conductor speaker.

For example, the environment microphone may be integrated in the speaker module 207 in FIG. 2. In such case, the environment microphone 207 collects sounds and the speaker or a connected host device processes the sounds like filter, recognize, amplify the sounds. In some embodiments, the sounds like gunshot may be filtered and recognized to find out which gun type is related to the gunshot sound. A distance or other event message may be converted corresponding sound sent to the person who wears the communication helmet. For example, "there is a gunshot at 11 o'clock position, which may be a AK-47 from an enemy" may be sent to a soldier or a policeman.

Under current sound recognition, other information may also be collected and generated based on raw data. This is particularly helpful for a soldier or a police man in a battle field. This is also helpful for a bicycle rider to be aware of an approaching car from behind.

The sound collected from a person's communication helmet may be sent to another communication helmet for processing together. In some other cases, multiple sound sources may be processed together to find more useful information therefrom.

A portable computer may be used for handling such processing, or the data are sent to a cloud server. Because current technology makes a mobile phone capable of processing complicated sound recognition, a distribution computation or a standalone computation may also be used, depending on different design needs.

In some embodiments, the event message is related to an explosion sound, as mentioned above. A helicopter, a tank, a ship, a closing car or other objects may also be put into an interest group to be analyzed.

By placing two sound collector devices like microphones, a position relative to the communication helmet may be estimated, just like human ears for detecting positions of a sound source.

In some embodiments, the communication helmet further includes an external device working with the processor for recognizing the environment sound. As mentioned above, the external device may be a portable host device also carried by the person who wears the communication helmet or may be another portable device held by another person or even a cloud server located in a distant place.

In some embodiments, the environment sounds collected by a plurality of the communication helmets are integrated with position data of the plurality of the communication helmets to determine an absolute position associated to the explosion sound. The absolute position is translated to multiple relative positions embedded in the event messages for the plurality of the communication helmets.

As mentioned above, a team of soldiers may each wear a communication helmet. These communication helmets may collect sounds or other information separately and then these information is exchanged among the communication helmets. By adding GPS (Global Positioning System) devices for providing absolute position information for multiple people who wear the communication helmets, the absolute positions of these people are analyzed by reference to sounds collected by multiple communication helmets and converted to relative information, e.g. "a gunshot at 11 o'clock" for a specific solder wearing the communication helmet.

Map information may also be integrated so that the audio information has map information like, "move right, there is a place to hide. A gunshot is from a left side forrest."

For military use, a set of communication helmets may be grouped and connected with a closed network, instead of communication over a public network. The processor may be operated over more than one networks and one of the networks may be a closed network only accessible by the communication helmets. The closed network is operated over encrypted technology so that other unauthenticated devices are unable to access data of the closed network.

In FIG. 2, the processor may have a manual switch 208 for entering the closed network when a mission is activated and entering a relative public network when the mission is finished.

In FIG. 2, the communication helmet may also include a pulse detector 209 connected to the processor for collecting heart pulse information of the human head. With such design, a team commander may have health information of his team members. The heart pulse information may be transmitted to another communication helmet.

In some embodiments, the processor provides an operation interface, e.g. via the manual switch 208 or a remote display (not shown) connected to the wireless circuit of the speaker module for setting a role in a team to the processor. The processor functions differently for different roles. For example, the speaker modules may be manually set and assigned to different team members. These team members may each have a different role, e.g. a captain or a shooter, and these communication helmets may be used with different functions and/or communication path settings, e.g. the communication topology, whose information should be transmitted to whose communication helmet.

In some embodiments, the processor includes a wireless circuit for processing wireless signals.

In some embodiments, the processor is selectively switched from multiple networks.

In some embodiments, there may be a manual switch for disabling a part of the multiple networks.

In some embodiments, a part of the multiple networks is disabled by sending a remote command to the processor. For example, when a soldier is dead, his helmet may be picked and used by an enemy. In such case, the communication helmet may be disabled for protecting other team members.

In some embodiments, the speaker module includes a microphone for collecting audio data from the human head.

The processor may also count how many bullets have been used and tell the soldier how many bullets are stilled existed.

In some embodiments, the audio data are converted to instructions, and the processed result of the instructions is replied via the bone conductive speaker. For example, a soldier, a rider or a police man may speak to issue commands, e.g. to turn on a machine, and the bone conductive speaker is used for sending feedback information, e.g. the machine is activated, to the person who wears the communication helmet.

In some embodiments, the processor handles wireless communication and data conversion for the bone conduction speaker.

In some embodiments, the helmet has a battery container for containing a battery supplying power to the speaker module. In such design, it is more comfortable when the speaker module has a less weight when its battery is moved and placed and protected in the helmet.

In some embodiments, the fixing belt has an electrical wire supplying power to the speaker module. In such design, the fixing belt may be woven or attached with power or signal lines used by the speaker module.

In some embodiments, biophysical data of the human head are collected as an authentication to operate the processor of the speaker module. For example, a radar wave may be sent to the human head of the person who wears the communication helmet and the response is used for authenticating the identity of the person.

One use of such function is to prevent unauthenticated users to use the communication helmets. Another use of such function is to dynamically correspond the communication helmet with the person who wears the communication helmet.

In addition to use vibrating wave to detect user head identity, optical image analysis may also be used for finding identify of the person who wears the communication helmet.

In some embodiments, the biophysical data are used for decrypting messages of the processor, e.g. as a key in a decryption computation or to encrypt communication information.

In some embodiments, the communication helmet may have an identification unit, like a card to be inserted into the sensor module or a RFID carrying a wireless information to be accessed by the speaker module, connected to a detachable identification module. The detachable identification module is attached to the speaker module for providing an identification message for the communication helmet.

In some embodiments, the processor selects at least one channel from multiple channels to generate the vibration wave. In other words, the processor may receive multiple channels and dynamically mix some of the channels converting to vibrating waves from the bone conductive speaker.

Another aspect of the invention is to provide a helmet speaker apparatus that has a contact part for engaging a cheek of a human head, a processor for providing sound data, and a bone conductor speaker connected to the contact part and the processor for generating a vibration wave corresponding to the sound data. The vibration wave is transmitted to a acoustic organ via the contact part and the cheek. The helmet speaker apparatus also has a module housing for being attached to an attaching structure of a fixing belt. The fixing belt has two belt ends connected to a helmet. The fixing belt and the helmet form a head container for fitting and protecting the human head.

The module housing may be water proof designed, with some exposed electrodes to be connected to a power source or to another device to work together.

Even without wearing the helmet, users may engage the helmet speaker apparatus to his cheek to hear sounds. With such design, it is easier to provide a robust design, or makes it more convenient to charge or replace when the helmet speaker apparatus is temporarily out of order.

Another aspect of the invention is to provide a battle field information system. The battle field information may include multiple communication helmets. Each communication helmet includes a helmet, a fixing belt and a speaker module, the speaker module being placed on the fixing belt with a contact part engaging to a cheek of a human head, a bone conductor speaker transmitting a vibrating wave corresponding to battle field data via the contact part to an acoustic organ of a human head wearing the communication helmet. A network device is used for the multiple communication helmets to communicate for utilizing environment sounds collected by the multiple communication helmets and dispatching environment messages via the bone conductor speakers of the multiple communication helmets.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings.

The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. A communication helmet, comprising:
a helmet with a head cavity for protecting a human head;
a fixing belt with two belt ends connecting to two sides of the helmet, the fixing belt and the helmet being together forming a head container for fitting the human head; and
a speaker module disposed on the fixing belt, the speaker module having a processor, a bone conductive speaker and a contact part, the contact part engaging a cheek of the human head when the human head being fit in the head container of the helmet and the fixing belt, the bone conductor speaker emitting a vibration wave corresponding to associated sound data from the processor, the vibration wave being transmitted to an acoustic organ of the human head via the contact part for transmitting information carried by the sound data to the human head.

2. The communication helmet of claim 1, wherein the fixing belt comprises an attaching structure for placing the speaker module and pressing the contact part of the speaker module to engage the cheek when the communication helmet is worn on the human head.

3. The communication helmet of claim 1, wherein the speaker module is connected to an environment microphone, the environment microphone collects an environment sound, an event message is generated by recognizing the environment sound and transmitted to the human head via the bone conductor speaker.

4. The communication helmet of claim 3, wherein the event message is related to an explosion sound.

5. The communication helmet of claim 4, further comprising an external device working with the processor for recognizing the environment sound.

6. The communication helmet of claim 5, wherein the environment sounds collected by a plurality of the communication helmets are integrated with position data of the plurality of the communication helmets to determine an absolute position associated to the explosion sound, the absolute position is translated to multiple relative positions embedded in the event messages for the plurality of the communication helmets.

7. The communication helmet of claim 6, wherein the position data of the plurality of the communication helmets are GPS positions only transmitted among the plurality of the communication helmets.

8. The communication helmet of claim 1, further comprising a pulse detector connected to the processor for collecting heart pulse information of the human head.

9. The communication helmet of claim 8, wherein the heart pulse information is transmitted to another communication helmet.

10. The communication helmet of claim 1, wherein the processor provides an operation interface for setting a role in a team to the processor, the processor functions differently for different roles.

11. The communication helmet of claim 1, wherein the processor comprises a wireless circuit for processing wireless signals.

12. The communication helmet of claim 11, wherein the processor is selectively switched from multiple networks.

13. The communication helmet of claim 12, further comprising a manual switch for disabling a part of the multiple networks.

14. The communication helmet of claim 12, wherein a part of the multiple networks is disabled by sending a remote command to the processor.

15. The communication helmet of claim 1, wherein the speaker module comprises a microphone for collecting audio data from the human head.

16. The communication helmet of claim 15, wherein the audio data are converted to instructions, and the processed result of the instructions is replied via the bone conductive speaker.

17. The communication helmet of claim 1, wherein the processor handles wireless communication and data conversion for the bone conduction speaker.

18. The communication helmet of claim 1, wherein the helmet has a battery container for containing a battery supplying power to the speaker module.

19. The communication helmet of claim 1, wherein the fixing belt has an electrical wire supplying power to the speaker module.

20. The communication helmet of claim 1, wherein biophysical data of the human head are collected as an authentication to operate the processor of the speaker module.

* * * * *